(12) United States Patent
Bureiko et al.

(10) Patent No.: US 7,597,719 B2
(45) Date of Patent: Oct. 6, 2009

(54) POLYMER THICKENED HAIR COLOURING AND BLEACHING COMPOSITIONS

(75) Inventors: Andrei Sergeevich Bureiko, Sunningdale (GB); Lee Arnold Schechtman, Fairfield, OH (US); Joseph Jay Kemper, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 50 days.

(21) Appl. No.: 11/888,173

(22) Filed: Jul. 31, 2007

(65) Prior Publication Data
US 2008/0029120 A1 Feb. 7, 2008

Related U.S. Application Data

(60) Provisional application No. 60/834,867, filed on Aug. 2, 2006.

(51) Int. Cl.
*A61Q 5/10* (2006.01)
(52) U.S. Cl. .................. 8/405; 8/435; 8/552; 8/554; 8/558; 8/606; 8/620; 8/101; 8/107; 8/111
(58) Field of Classification Search .............. 8/405, 8/435, 552, 554, 555, 558, 606, 620, 101, 8/107, 111
See application file for complete search history.

(56) References Cited

U.S. PATENT DOCUMENTS

| | | | | |
|---|---|---|---|---|
| 4,994,088 | A * | 2/1991 | Ando et al. | 8/426 |
| 5,171,808 | A | 12/1992 | Ryles et al. | |
| 6,260,556 | B1 * | 7/2001 | Legrand et al. | 132/208 |
| 7,204,861 | B2 | 4/2007 | Marsh et al. | |
| 2003/0175233 | A1 | 9/2003 | Hossel et al. | |
| 2004/0083557 | A1 | 5/2004 | Au et al. | |
| 2004/0098814 | A1 | 5/2004 | Au et al. | |
| 2004/0098816 | A1 | 5/2004 | Au et al. | |
| 2004/0237218 | A1 * | 12/2004 | Marsh et al. | 8/405 |

FOREIGN PATENT DOCUMENTS

| | | |
|---|---|---|
| EP | 217274 | 6/1988 |
| EP | 435012 | 4/1994 |
| EP | 1048290 | 11/2000 |
| EP | 1396508 | 3/2004 |
| EP | 1106166 | 3/2006 |
| EP | 1064924 | 4/2006 |
| JP | 2001206825 | 7/2001 |
| JP | 2004091355 | 3/2004 |
| JP | 2004262885 | 9/2004 |
| WO | WO 0128508 | 4/2001 |
| WO | WO04014328 | 2/2004 |

OTHER PUBLICATIONS

PCT International Search Report, Feb. 14, 2008, 4 pages.
U.S. Appl. No. 11/827,159, Jul. 11, 2007, Application from co-pending application Case No. CM3119, 35 pages.
U.S. Appl. No. 11/789,451, Apr. 24, 2007, Office Actions rejections/objections from co-pending application Case No. CM 3062, 12 pages.
U.S. Appl. No. 11/715,188, Mar. 07, 2007, Office Actions rejections/objections from co-pending application Case No. CM 3064, 7 pages.
U.S. Appl. No. 11/706,703, Feb. 15, 2007, Office Actions rejections/objections from co-pending application Case No. CM 3059M, 10 pages.
U.S. Appl. No. 11/414,575, Apr. 28, 2006, Office Actions rejections/objections from co-pending application Case No. CM2965, 25 pages.
U.S. Appl. No. 11/293,570, Dec. 02, 2005, Office Actions rejections/objections from co-pending application Case No. CM 2923M, 26 pages.
U.S. Appl. No. 11/293,589, Dec. 02, 2005, Office Actions rejections/objections from co-pending application Case No. CM 2924M, 33 pages.
U.S. Appl. No. 11/293,596, Dec. 02, 2005, Office Actions rejections/objections from co-pending application Case No. CM2925M, 19 pages.
U.S. Appl. No. 11/292,129, Dec. 01, 2005, Office Actions rejections/objections from co-pending application Case No. CM2921M, 28 pages.
U.S. Appl. No. 11/291,666, Dec. 01, 2005, Office Actions rejections/objections from co-pending application Case No. CM2922M, 44 pages.
U.S. Appl. No. 11/233,277, Sep. 22, 2005, Office Actions rejections/objections from co-pending application Case No. CM2911M, 16 pages.

* cited by examiner

*Primary Examiner*—Eisa B Elhilo
(74) *Attorney, Agent, or Firm*—Melissa G. Krasovec

(57) ABSTRACT

The present invention relates to hair coloring and hair bleaching compositions comprising at least one oxidizing agent and a specified cross linked amphoteric polymeric thickener and preferably a source of carbonate ion. The compositions surprisingly provide improved hair colorant and bleaching compositions which deliver improved lift, lightening and color delivery whilst minimizing damage which are easy to manufacture and have long shelf life stability.

19 Claims, No Drawings

POLYMER THICKENED HAIR COLOURING AND BLEACHING COMPOSITIONS

CROSS REFERENCE TO RELATED APPLICATION

This application claims the benefit of U.S. Provisional Application No. 60/834,867, filed Aug. 2, 2006.

FIELD OF THE INVENTION

The present invention relates to hair colourant and bleaching compositions.

BACKGROUND OF THE INVENTION

The permanent alteration of the colour of keratinous fibres, in particular human hair, by the application of hair dyes is well known. In order to provide the consumer with the hair colour and the intensity of colour desired, a very complex chemical process is utilized. Permanent hair dyeing formulations typically comprise oxidative hair dye precursors, which can diffuse into the hair through the cuticle and into the cortex where they can then react with each other and suitable oxidising agents to form the end dye molecules. Due to the larger size of these resultant molecules they are unable to readily diffuse out of the hair during subsequent washing with water and/or detergents; hence delivering a consumer-desired permanency of colour. This reaction typically takes place in an aggressive environment at approximately pH 10 in the presence of an alkalizing agent and in the presence of an oxidizing agent. Moreover, the consumer repeats this process regularly in order to maintain the desired hair colour and shade and the intensity of colour and to ensure continual, even coverage of the hair including coverage of new hair growth.

The manufacturer of such products is also required to work within a large number of constraints. Since these products are being placed in direct contact with the consumers' skin, the potential exists for accidental contact with the eye or for ingestion (for example), which can occur during the dyeing process. Therefore, the formulation must meet rigorous safety requirements and not induce any allergic reactions. In addition to meeting these requirements, the products must also be optically and olfactory pleasing to the consumer. In particular, the products also need to meet certain physical parameters in order to ensure that the product can be easily applied to the hair by the consumer to provide the desired effect, without unintentional staining of the consumers' clothes, skin or other objects.

The manufacturer is also required to provide the hair colouring consumer a large range of different resulting colours. Some consumers may just wish to enhance the natural colour of the hair, whilst others may wish to cover grey or completely alter the hair colour to a different natural appearing hair colour or a 'synthetic' appearing hair colour. Consequently, the manufacturer may provide over twenty different formulations, of varying colours and shades, to address the range of consumer specific needs. These formulations have to be individually formulated and are typically complex formulae containing a mixture of different dye compounds. As a result the manufacture of such product ranges can be costly and complex.

However, despite the fact that commercial hair dyeing products have been available for many years, the products still exhibit a number of consumer-related deficiencies.

Typically permanent hair dye products will contain an alkali, typically a source of ammonia. This serves the purpose of swelling the hair allowing the entry of the dye precursor molecules into the hair and also improves the lightening effect of the oxidising agent, which is typically hydrogen peroxide. However, ammonia is also volatile and its associated odour is extremely unpleasant to the consumers' of such products, particularly as these hair dye products are used in close proximity to the nasal region. Hence, it would be highly desirable to provide an oxidative hair colouring and/or bleaching composition, which delivers the consumer required lightening level and colour, but which has reduced or eliminated the detectable ammonia odour.

In fact another deficiency area in current hair colouring products is the provision of hair colouring products which deliver the required hair lightening effect. Delivering the required level of lightening is particularly important in order to provide the full range of colour shades demanded by the consumer, especially for blonde shades and grey coverage. Such products pose particular difficulties to the manufacturer, as they usually require the use of high levels of oxidising agent and ammonia in order to deliver the required lightening effect. However, in additional to the problems associated with the presence of high levels of ammonia in these products, as discussed herein above, the presence of these high levels of ammonia and/or oxidizing agent also affect the condition of the hair and may in some cases induce mild skin irritation on the scalp. In particular, the hydrophilicity of the hair surface is increased during the colouring process, which alters the sensory perception of the hair and its overall manageability during and, immediately after colouring, and during the subsequent wash and styling cycles until the next colourant application. Hence, it would also be highly desirable to provide an oxidative hair colouring and/or bleaching composition which delivers the required lightening and/or colour without unnecessary hair damage.

A number of attempts have been described in the literature to address at least some of the above identified improvement areas. For example the use of carbonate has been described in the following hair colouring art. EP 435 012 describes hair-dyeing compositions, which require a short dyeing time, create little damage to hair, and no irritating odour after dyeing comprising a carbonate source, a non odour generating alkali hydrogen peroxide and a buffer solution. Similarly EP 1 106 166 describes hair dye compositions comprising ammonia, carbonate (other than ammonia salt), transition metal salt and chelating agent which do not give off an irritating odour, have low skin irritation and can change the hair colour into a lighter tone in a short time. WO01/28508 describes hair colouring formulations comprising oxidising agents and ammonia carbonate or carbamate which deliver improved bleaching and colouring with reduced odour and hair damage without the need for buffering agents, pH modifiers or hair swelling agents. JP01206825 describes a low pungent hair colouring composition comprising ammonia, ammonium salt and carbonate. US2004/0083557 describes hair colouring compositions comprising an oxidative hair dye precursor, a metal cyanate, an alkalizing agent and an oxidizing agent and preferably a metal bicarbonate salt in order to provide good colour lift and low odour.

WO04/014328 describes one step hair colouring compositions comprising peroxide oxidizing agents, specific oxidizing agents and at least one water soluble carbonate releasing salts which more effectively deliver colour wherein the composition is applied for a period of from 2 to 60 minutes. US2004/0098814 describes a method of permanently colouring hair whereby the hair is subjected to a number of consecutive short treatments whereby the treatment comprises a dye intermediate in a shampoo or conditioner base, a water soluble carbonate releasing salt and a water soluble ammonium salt. US2004/0098816 also describes a method for the gradual permanent colouring of hair which includes subjecting the hair to a number of treatments having a set time interval between them, wherein the treatment compositions comprise ammonium carbonate in combination with a chelant.

However it has now been found that the use of hydrogen peroxide and carbonate hair colourant systems, results in difficulties in manufacturing. This problem is particularly manifest for compositions which have high levels of peroxide and carbonate which are desirable to provide high levels of lift. Moreover in order to provide a product which the consumer can easily apply to the hair without dripping onto the skin, clothes or bathroom surfaces, hair colourant products are designed such that the composition has a certain required viscosity. This is either achieved by providing the dye composition and the oxidizing composition as so called thin-thin type liquid formulations which are thickened upon mixing or where at least one of the components, either the dye composition or the oxidizing composition, preferably the dye composition, is provided as a thickened formulation which thickens the total composition upon mixing.

Carbonate systems in the art herein above describe numerous materials suitable for thickening. However these materials have been found not to sufficiently thicken compositions comprising high levels of carbonate resulting in product instability or unsatisfactory viscosity. Also many polymers disclosed in carbonate systems are of anionic nature and hence not compatible with commonly utilized cationic conditioning agents. Hence it would be desirable to provide a hair colorant composition which incorporates high levels of carbonate without compromising the product stability, ease of manufacture or conditioning properties of the composition.

Another particularly critical performance area for the consumer is the provision of the desired resultant colour and also the effective coverage of grey hair. Indeed, whilst the amount of grey hair to be coloured varies considerably from consumer to consumer, the resultant overall appearance of the coloured hair demanded by the consumer should be nearly identical for the naturally pigmented hair and the grey hair on head, with the added requirement that the initial coverage is maintained during the post dyeing washing and drying cycle.

Hence, it would be further desirable to provide the consumer with a hair colourant, providing improved lift and lightening and improved colour delivery, uptake and durability and which is easy to manufacture, delivering the required viscosity and is shelf life stable.

It has now been surprisingly found that oxidative hair colouring compositions comprising an oxidising agent, and a specific cross linked amphoteric polymeric thickener as defined herein and preferably a source of carbonate ions can be formulated as stable thickened systems. Moreover the compositions exhibit low odour and deliver a high level of lift and lightening equal to the currently utilized ammonia/peroxide systems, whilst reducing the concentration of peroxide and reducing the hair fibre damage. Moreover, the compositions of the present invention are compatible with current dyes and dye precursor systems and result in improved lift and lightening for blond shades, excellent dye deposition and colour and improved grey coverage. In addition the compositions of the present invention are compatible with a variety of conditioning agents, including the particularly desirable cationic polymers and aminosilicones.

Polymers have been described in the art for a variety of applications. For example U.S. Pat. No. 5,171,808 describes cross linked anionic and amphoteric polymeric micropar-ticles as flocculating agents. EP 217274 describes hair cosmetic compositions comprising amphoteric polymers and water soluble salts to provide improved hair style retention without reducing hair feel. EP1396508 discloses the production of aqueous dispersions of cationic homo- and copolymers using amphoteric colloids for a variety of applications including hair and skin cosmetics. EP1064924 describes a copolymer made by radical initiated copolymerization of a mixture containing an N-vinylimidazole or allylamine monomer as an additive for skin cosmetics or dermatological preparations. US2003/0175233 discloses hair cosmetic agents comprising a polymer obtainable by free-radically initiated copolymerization and a relaxer. However, none of the prior art documents describe or teach the use of the presently claimed cross linked amphoteric polymers for oxidative hair colouring applications

SUMMARY OF THE INVENTION

The present invention relates to a hair colouring or bleaching composition comprising
at least one oxidizing agent and
at least one cross-linked amphoteric polymer, wherein said polymer comprises
1) at least one first monomer of formula (I)

$$R_1-CH=CR_2-CO-Y_1 \quad (I)$$

where $R_1$ is independently selected form hydrogen atom, a methyl radical and a COOH group, $R_2$ is independently selected from a hydrogen atom, a methyl radical and a $CH_2COOH$ group, and $Y_1$ is selected from an OH group and a $NHC(CH_3)_2CH_2SO_3H$ group,
2) at least one second monomer selected from diallyldimethylammonium salt, 3-methyl-1-vinylimidazolium salt, or the monomers of formula (II)

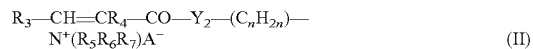

$$R_3-CH=CR_4-CO-Y_2-(C_nH_{2n})-N^+(R_5R_6R_7)A^- \quad (II)$$

wherein $R_3$ and $R_4$, which are identical or different, are each selected from a hydrogen atom and a methyl radical; $R_5$, $R_6$ and $R_7$, which are identical or different, are each selected from linear or branched alkyl radical having from 1 to 6 carbon atoms; $Y_2$ is selected from an NH group and an oxygen atom; n is an integer from 2 to 5; and $A^-$ is an anion selected from anions derived from organic and inorganic acids, and
3) at least one cross-linking agent.

A further embodiment of the present invention relates to a hair colouring or bleaching kit comprising
i) an individually packaged oxidizing component comprising at least one source of hydrogen peroxide
ii) an individually packaged second component comprising at least one cross-linked amphoteric polymer, wherein said polymer comprises
1) at least one monomer of formula (I)

$$R_1-CH=CR_2-CO-Y_1 \quad (I)$$

where $R_1$ is independently selected from hydrogen atom, a methyl radical and a COOH group, $R_2$ is independently selected from a hydrogen atom, a methyl radical and a $CH_2COOH$ group, and $Y_1$ is independently selected from an OH group and a $NHC(CH_3)_2CH_2SO_3H$ group,
2) at least second one monomer selected from diallyldimethylammonium salt, 3-methyl-1-vinylimidazolium salt, or the monomers of formula (II)

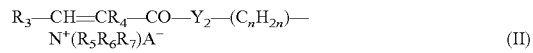

$$R_3-CH=CR_4-CO-Y_2-(C_nH_{2n})-N^+(R_5R_6R_7)A^- \quad (II)$$

Wherein $R_3$ and $R_4$, which are identical or different, are each selected from a hydrogen atom and a methyl radical; $R_5$, $R_6$ and $R_7$, which are identical or different, are each selected from a linear or branched alkyl radical having from 1 to 6 carbon atoms; $Y_2$ is selected from an NH group and an oxygen atom; n is an integer from 2 to 5; and $A^-$ is an anion selected from anions derived from organic and inorganic acids and 3) at least one cross-linking agent.

An alternative embodiment relates to a hair colouring or bleaching kit comprising i) an individually packaged oxidizing component comprising
   a) at least one source of hydrogen peroxide, and
   b) at least one cross-linked amphoteric polymer, wherein said polymer comprises 1) at least one first monomer of formula (I)

$$R_1\text{---}CH\!=\!CR_2\text{---}CO\text{---}Y_1 \quad (I)$$

where $R_1$ is independently selected form hydrogen atom, a methyl radical and a COOH group, $R_2$ is independently selected from a hydrogen atom, a methyl radical and a $CH_2COOH$ group, and $Y_1$ is selected from an OH group and a $NHC(CH_3)_2CH_2SO_3H$ group, 2) at least one second monomer selected from diallyldimethylammonium salt, 3-methyl-1-vinylimidazolium salt, or the monomers of formula (II)

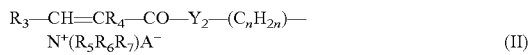

$$R_3\text{---}CH\!=\!CR_4\text{---}CO\text{---}Y_2\text{---}(C_nH_{2n})\text{---}$$
$$N^+(R_5R_6R_7)A^- \quad (II)$$

Wherein $R_3$ and $R_4$, which are identical or different, are each selected from a hydrogen atom and a methyl radical; $R_5$, $R_6$ and $R_7$, which are identical or different, are each selected from linear or branched alkyl radical having from 1 to 6 carbon atoms; $Y_2$ is selected from an NH group and an oxygen atom; n is an integer from 2 to 5; and $A^-$ is an anion selected from anions derived from organic and inorganic acids 3) at least one cross-linking agent, ii) an individually packaged second component, preferably comprising a source of carbonate ions, carbamate ions or hydrogencarbonate ions and mixtures thereof.

In a preferred embodiment of the present invention the compositions upon mixing said components comprise at least 0.1 mol/l of a source of carbonate ions, carbamate ions, hydrogencarbonate ions or peroxymonocarbonate ions and mixtures thereof.

A further embodiment relates to a method of colouring or bleaching hair comprising the steps of applying the said composition to the hair and in a further aspect the present invention relates to a method of applying the compositions of the present invention to the hair and leaving the compositions on the hair for up to about 60 minutes, and subsequently rinsing the compositions from the hair.

Another aspect of the present invention relates to a method of sequential oxidative hair colouring or hair bleaching comprising the steps of at least two sequential oxidative hair colour or hair bleaching treatments wherein the time period between each treatment is from about 1 day to about 60 days, and wherein each treatment comprises the steps of providing a composition of the present invention, then applying said composition to the hair and retaining said composition on the hair for a time period of less than about 20 minutes and subsequently rinsing said composition from the hair.

DETAILED DESCRIPTION OF THE INVENTION

While the specification concludes with claims, which particularly point out and distinctly claim the invention, it is believed the present invention will be better understood from the following description.

As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention.

All percentages are by weight of the total composition unless specifically stated otherwise. When more than one composition are used during a treatment, the total weight to be considered is the total weight of all the compositions applied on the hair simultaneously (i.e. the weight found "on head") unless otherwise specified. All ratios are weight ratios unless specifically stated otherwise. All molar concentrations are by volume of the total composition and presented as number of moles of component(s) in one liter of the composition, or "mol/l". When more than one composition are used during a treatment, the total volume to be considered is the total volume of all the compositions applied on the hair simultaneously (i.e. the volume found "on head") unless otherwise specified.

Cross-Linked Amphoteric Polymer

According to the present invention, the hair colouring and bleaching compositions comprise at least one cross-linked amphoteric polymer thickener.

Those skilled in the art will recognize that polymer thickening systems usually provide thickening by chain entanglement, network formation or micro-gel swelling. These systems usually have gel appearance and feel and are thus strongly desirable. However, polymer thickeners can be salted out by high levels of other components in the compositions such as carbonate salts, leading to viscosity loss. Further, osmotic swelling of micro-gel particles made of, for example, cross-linked polymers is suppressed by carbonate salt addition, also resulting in viscosity loss.

Even further, other components of typical colouring composition such as solvents and oxidative or pre-formed dyes, affect polymer properties and make selection of suitable polymers in carbonate systems particularly difficult. Further, in one of the embodiment of this invention, polymers have to be incorporated into a liquid composition i.e a composition comprising at least 10% by weight of a solvent such as water, together with carbonate salts, and provide shelf life stability of such liquid composition. In one of the alternative embodiments, polymers have to be incorporated into a liquid composition containing an oxidizing agent and have to provide shelf life stability of such liquid composition.

Even further, it is often desirable that polymers provide little viscosity until two parts of the colouring or bleaching composition are mixed by consumers, at which point polymers will be "triggered" to build high viscosity of the so called thin-thin type liquid formulations.

Surprisingly, it has now been found that by the required specific selection of the polymer thickener, thickening efficiency can be achieved. Without being bound by theory, it is believed that the cross-linked amphoteric polymer thickeners described in this invention form partially or completely internally neutralized micro-gel, which exhibits additional swelling upon addition of electrolyte for example carbonate salts, thus providing required "triggered" thickening.

According to the present invention the hair coloring or bleaching compositions and kits thereof comprise at least one cross-linked amphoteric polymer comprising
1) at least one first monomer of formula (I)

$$R_1—CH=CR_2—CO—Y_1 \quad (I)$$

where $R_1$ is independently selected from hydrogen atom, a methyl radical and a COOH group, $R_2$ is independently selected from a hydrogen atom, a methyl radical and a $CH_2COOH$ group, and $Y_1$ is selected from an OH group and a $NHC(CH_3)_2CH_2SO_3H$ group,
2) at least one second monomer selected from diallyldimethylammonium salt, 3-methyl-1-vinylimidazolium salt, or monomers of formula (II)

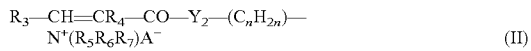

$$R_3—CH=CR_4—CO—Y_2—(C_nH_{2n})—$$
$$N^+(R_5R_6R_7)A^- \quad (II)$$

wherein $R_3$ and $R_4$, which are identical or different, are each selected from a hydrogen atom and a methyl radical; $R_5$, $R_6$ and $R_7$, which are identical or different, are each selected from a linear or branched alkyl radical having from 1 to 6 carbon atoms; $Y_2$ is selected from an NH group and an oxygen atom; n is an integer from 2 to 5; and $A^-$ is an anion selected from anions derived from organic and inorganic acids and
3) at least one cross-linking agent.

Preferable first monomers of formula (I) for use herein comprise acrylic acid or methacrylic acid or mixtures thereof. Preferable second monomers of formula (II) comprise diallyldimethylammonium chloride, 3-methyl-1-vinylimidazolium chloride and 3-methylacryolylamidopropylthrimethylammonium chloride and mixtures thereof. Preferred cross-linking agents are 1,3-diallylurea, N,N-diallylacrylamide, N,N-methylenebisacrylamide, pentaerythritol triallylether, triallylamine, tetraallylammonium chloride and methyltriallylammonium chloride and mixtures thereof. A particularly preferred cross-linking agent is 1,3-diallylurea which gives additional resistance of the polymer to the high levels of oxidizing agents.

The polymers comprise from 40 to 80 mol %, preferably from 70 to 80 mol %, of the first monomers and from 20 to 60 mol %, preferably from 20 to 30 mol %, of the second monomers, and from 0.01 to 5 mol %, preferably from 0.1 to 1 mole % of the cross-linking agent.

According to the present invention the compositions comprise from about 0.1% to about 20% by weight, preferably from about 1% to about 7% by weight, and most preferably from about 2% to about 5% by weight of the cross-linked amphoteric polymers.

Oxidizing Agent

The compositions according to the present invention comprise or are used in combination with a composition that comprises at least one source of an oxidizing agent. Preferred oxidizing agents for use herein are water-soluble peroxygen oxidizing agents. "Water-soluble" as defined herein means that in standard condition at least 0.1 g, preferably 1 g, more preferably 10 g of said oxidizing agent can be dissolved in 1 liter of deionized water. The oxidizing agents are valuable for the initial solubilisation and decolorisation of the melanin (bleaching) and accelerate the oxidation of the oxidative dye precursors (oxidative dyeing) in the hair shaft.

Any oxidizing agent known in the art may be utilized in the present invention. Preferred water-soluble oxidizing agents are inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Alkyl and aryl peroxides, and/or peroxidases may also be used. Mixtures of two or more such oxidizing agents can be used if desired. The oxidizing agents may be provided in aqueous solution or as a powder which is dissolved prior to use. Preferred for use in the compositions according to the present invention are hydrogen peroxide, percarbonate (which may be used to provide a source of both oxidizing agent and carbonate ions), persulphates and combinations thereof.

According to the present invention the compositions comprise from about 0.1% to about 10% by weight, preferably from about 1% to about 7% by weight, and most preferably from about 2% to about 5% by weight of an oxidizing agent.

Carbonate Ion Source

In a preferred embodiment of the present invention the compositions further comprise a source of carbonate ions or carbamate ions or hydrogen carbonate ions or peroxymoncarbonate ions. These ions are typically formed in-situ from the reaction between a source of hydrogen peroxide and carbonate ion. According to the present invention the compositions thus preferably comprise at least 0.1 mol/l of source of carbonate ions or carbamate ions or hydrogencarbonate ions or peroxymonocarbonate ions or any mixture thereof. This amount can be achieved for example by addition of at least about 0.97% (volume percent) of ammonium carbonate (molecular weight equals to 96.09 g/mol) to the composition of invention or, for example, by addition of about 0.50% (volume percent) of Ammonium Carbonate and at least about 0.50% (volume percent) of Potassium Hydrogen Carbonate (molecular weight equals 100.12 g/mol). The compositions of the present invention preferably comprises from about 0.2 mol/l to about 2.0 mol/l, more preferably from about 0.4 mol/l to about 1.5 mol/l of the source of said ions.

It should also be understood that when the composition of the invention is used as a hair colouring or bleaching kit comprising and individually packaged oxidizing component and an individually packaged second component such as a bleaching or colouring component, the concentration of the source of the said ions will be increased in the said bleaching or colouring component proportionally to the mixing ratio of components in order to achieve the concentration of at least 0.1 mol/l upon mixing of the components to provide the composition applied to the hair.

Any source of these ions may be utilized. Suitable sources for use herein include sodium, potassium, lithium, calcium, magnesium, barium, ammonium salts of carbonate, carbamate and hydrogencarbonate ions and mixtures thereof such as sodium carbonate, sodium hydrogen carbonate, potassium carbonate, potassium hydrogen carbonate, lithium carbonate, calcium carbonate, magnesium carbonate, barium carbonate, ammonium carbonate, ammonium hydrogen carbonate and mixtures thereof. Percarbonate salts may also be utilized to provide both the source of carbonate ions and oxidizing agent. Preferred sources of carbonate ions, carbamate and hydrogencarbonate ions are sodium hydrogen carbonate, potassium hydrogen carbonate, ammonium carbamate and mixtures thereof.

The compositions of the present invention preferably have a pH up to and including about pH 9.3. Preferably, the compositions of the present invention have a pH of from about 9.3 to about 7.5, more preferably from about 9.3 to about 8.4 and most preferably from about 9.2 to about 8.5 and even more preferably about pH 9.0. Preferably, the compositions of the present invention are prepared such that prior to application to the hair fibres the pH of the composition is no greater than about pH 9.3. However, in another embodiment of the present invention the compositions may be formulated such that the pH is up to 9.3 during the time period of application of the composition to the hair fibres prior to removal therefrom. Preferably, the pH is up to about 9.3 for at least about 50% of the time period, preferably at least about 70%, most preferably at least about 80% of the time period of application of the composition to the hair. More preferably, the pH of the composition is up to about pH 9.3 within about 10 minutes, preferably within about 5 minutes of application to the hair fibres.

The pH of the compositions can be determined by using either a Mettler Toledo MP220 or a MP225 pH equipment, fitted with a standard laboratory pH electrode. The equipment is calibrated before each use using standard calibration buffers and using standard calibration procedure.

Additional components

The compositions of the present invention may further comprise additional ingredients which include, but are not limited to, hair dyeing agents such as oxidative dye precursors, non-oxidative dyes, solvents, enzymes, surfactants, conditioning agents, carriers, antioxidants, stabilizers, chelants, perming actives, perfume, reducing agents (thiolactic acid), hair swelling agents and/or polymers. Some of these additional components are detailed hereafter.

Radical Scavenger

According to the present invention the compositions may comprise a source of radical scavenger. As used herein the term radical scavenger refers to a species that can react with a radical, preferably a carbonate radical to convert the radical species by a series of fast reactions to a less reactive species. The radical scavenger is also preferably selected such that it is not an identical species as the alkalising agent and ins present in an amount sufficient to reduce the damage to the hair during the colouring/bleaching process. The compositions of the present invention comprise from about 0.1% to about 10% by weight, preferably from about 1% by weight to about 7% by weight of a radical scavenger.

Preferred radical scavengers are selected from the classes of alkanolamines, amino sugars, amino acids, esters of amino acids and mixtures thereof. Particularly preferred compounds are: monethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentol, 1-amino-4-pentanol, 3-amino-2-methylpropan-1-ol, 1-amino-2methylpropan-2-ol3-aminopropane-1-2-diol, glucosamine, N-acetylglucosamine, glycine, arginine, lysine, praline, glutamine, histidine, sarcosine, serine, glutamic acid, tryptophan, and mixtures thereof and the salts such as potassium, sodium and ammonium salts thereof and mixtures thereof. Especially preferred compounds are glycine, sarcosine, tysine, serine, 2-methoxyethylamine, glucosamine, glutamic acid, morpholine, piperidine, ethylamine, 3-amino-1-propanol and mixtures thereof.

Source of ammonium ions

According to the present invention the composition may optionally comprise at least one source of ammonium ions and or ammonia. Any source of ammonium ions is suitable for use herein. Preferred sources include ammonium chloride, ammonium sulphate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof. Particularly preferred are ammonium carbonate, ammonium carbamate, ammonia and mixtures thereof. In a particularly preferred embodiment of the present invention, the ammonium ion source and the carbonate ion sources are provided by a single source such as ammonium carbonate, ammonium hydrogen carbonate, ammonium carbamate or mixtures thereof. Preferably, if present, the ammonium ions and carbonate ions are present in the composition at a weight ratio of from 3:1 to 1:10, preferably 2:1 to 1:5.

The compositions of the present invention may comprise from about 0.1% to about 10% by weight, preferably from about 0.5% to about 5%, most preferably from about 1% to about 3% of ammonium ions.

Hair dyes

The hair compositions of the present invention are preferably hair colouring compositions which comprise oxidative dyeing compositions. Such compositions comprise oxidative hair dye precursors (also known as primary intermediates) that will deliver a variety of hair colors to the hair. These small molecules are activated by the oxidizing agent and react with further molecules to form a larger colored complex in the hair shaft.

The precursors can be used alone or in combination with other precursors, and one or more can be used in combination with one or more couplers. Couplers (also known as color modifiers or secondary intermediates) are generally colorless molecules that can form colors in the presence of activated precursors, and are used with other precursors or couplers to generate specific color effects or to stabilize the color. The choice of precursors and couplers will be determined by the color, shade and intensity of coloration that is desired. The precursors and couplers can be used herein, singly or in combination, to provide dyes having a variety of shades ranging from ash blonde to black.

These compounds are well known in the art, and include aromatic diamines, aminophenols, aromatic diols and their derivatives (a representative but not exhaustive list of oxidation dye precursor can be found in Sagarin, "Cosmetic Science and Technology", "Interscience, Special Edn. Vol. 2 pages 308 to 310). Suitable dyes for use herein include:—

1,7-Dihydroxynaphthalene (1,7-NAPHTHALENEDIOL), 1,3-Diaminobenzene (m-PHENYLENEDIAMINE), 1-Methyl-2,5-diaminobenzene (TOLUENE-2,5-DIAMINE), 1,4-Diaminobenzene (p-PHENYLENEDIAMINE), 1,3-Dihydroxybenzene (RESORCINOL), 1,3-Dihydroxy-4-chlorobenzene, (4-CHLORORESORCINOL), 1-Hydroxy-2-aminobenzene, (o-AMINOPHENOL), 1-Hydroxy-3-aminobenzene (m-AMINOPHENOL), 1-Hydroxy-4-amino-benzene (p-AMINOPHENOL), 1-Hydroxynaphthalene (1-NAPHTHOL), 1,5-Dihydroxynaphthalene (1,5-NAPHTHALENEDIOL), 2,7-Dihydroxy-naphthalene (2,7-NAPHTHALENEDIOL), 1-Hydroxy-2,4-diaminobenzene (4-DIAMINOPHENOL), 1,4-Dihydroxybenzene (HYDROQUINONE), 1-Hydroxy-4-methylaminobenzene (p-METHYLAMINOPHENOL), 6-Hydroxybenzo-morpholine (HYDROXYBENZOMORPHOLINE), 1-Methyl-2-hydroxy-4-aminobenzene (4-AMINO-2-HYDROXY-TOLUENE), 3,4-Diaminobenzoic acid (3,4-DIAMINOBENZOIC ACID), 1-Methyl-2-hydroxy-4-(2'-hydroxyethyl)aminobenzene (2-METHYL-5-HYDROXY-ETHYLAMINO-PHE- NOL), 1,2,4-Trihydroxybenzene (1,2,4-TRIHYDROXY-BENZENE), 1-Phenyl-3-methylpyrazol-5-on (PHENYL METHYL PYRAZOLONE), 1-(2'-Hydroxyethyloxy)-2,4-diaminobenzene (2,4-DIAMINOPHENOXY-ETHANOL HCL), 1-Hydroxy-3-amino-2,4-dichlorobenzene (3-AMINO-2,4-DICHLORO-PHENOL), 1,3-Dihydroxy-2-methylbenzene (2-METHYLRESORCINOL), 1-Amino-4-bis-(2'-hydroxyethyl)aminobenzene (N,N-BIS(2-HY-DROXY-ETHYL)-p-PHENYLENE-DIAMINE), 2,4,5,6-Tetraminopyrimidine (HC Red 16), 1-Hydroxy-3-methyl-4-aminobenzene (4-AMINO-m-CRESOL), 1-Hydroxy-2-amino-5-methylbenzene (6-AMINO-m-CRESOL), 1,3-Bis-(2,4-Diaminophenoxy)propane (1,3-BIS-(2,4-DIAMINO-PHENOXY)-PROPANE), 1-(2'-Hydroxyethyl)-2,5-diaminobenzene (HYDROXYETHYL-p-PHENYLENE DIAMINE SULPHATE), 1-Methoxy-2-amino-4-(2'-hydroxyethylamino)benzene (2-AMINO-4-HYDROXY-ETHYLAMINOANISOLE), 1-Hydroxy-2-methyl-5-amino-6-chlorobenzene (5-AMINO-6-CHLORO-o-CRESOL), 1-Hydroxy-2-amino-6-methylbenzene (6-AMINO-o-CRESOL), 1-(2'-Hydroxyethyl)-amino-3,4-methylene-dioxybenzene (HYDROXYETHYL-3,4-METHYLENE-DIOXY-ANILINE HCl), 2,6-Dihydroxy-3,4-dimethylpyridine (2,6-DIHYDROXY-3,4-DIMETHYLPYRIDINE), 3,5-Diamino-2,6-dimethoxypyridine (2,6-DIMETHOXY-3,5-PYRIDINEDIAMINE), 5,6-Dihydroxyindole (,DIHYDROXY-INDOLE), 4-Amino-2-aminomethylphenol (2-AMINOETHYL-p-AMINO-PHENOL HCl), 2,4-Di-amino-5-methylphenetol (2,4-DIAMINO-5-METHYL-PHENETOLE HCl), 2,4-Diamino-5-(2'-hydroxyethyloxy) toluene (2,4-DIAMINO-5-METHYLPHENOXYETHANOL HCl), 5-Amino-4-chloro-2-methylphenol (5-AMINO-4-CHLORO-o-CRESOL), 4-Amino-1-hydroxy-2-(2'-hydroxyethylaminomethyl)benzene (HYDROXYETHYLAMINOMETHYL-p-AMINO PHENOL HCl), 4-Amino-1-hydroxy-2-methoxymethylbenzene (2-METHOXYMETHYL-p-AMINOPHENOL HCl), 1,3-Bis(N(2-Hydroxyethyl)N(4-amino-phenyl)amino)-2-propanol (HYDROXYPROPYL-BIS-(N-HYDROXY-ETHYL-p-PHENYLENEDIAMINE)HCL), 6-Hydroxyindole (6-HYDROXY-INDOLE), 2,3-Indolinedione (ISATIN), 3-Amino-2-methylamino-6-methoxypyridine (HC BLUE NO. 7), 1-Phenyl-3-methyl-5-pyrazolone-2,4-dihydro-5,2-phenyl-3H-pyrazole-3-one, 2-Amino-3-hydroxypyridine (2-AMINO-3-HYDROXYPYRIDINE), 5-Amino-salicylic acid, 1-Methyl-2,6-bis(2-hydroxy-ethylamino)benzene (2,6-HYDROXYETHYLAMINOTOLUENE), 4-Hydroxy-2,5,6-triaminopyrimidine (2,5,6-TRIAMINO-4-PYRIMIDINOL SULPHATE), 2,2'-[1,2-Ethanediyl-bis-(oxy-2,1-ethanediyloxy)]-bis-benzene-1,4-diamine (PEG-3,2',2'-DI-p-PHE-NYLENEDIAMINE), 5,6-Dihydroxyindoline (DIHY-DROXYINDOLINE), N,N-Dimethyl-3-ureidoaniline (m-DIMETHYL-AMINO-PHENYLUREA), 2,4-Diamino-5-fluortoluenesulfatehydrate (4-FLUORO-6-METHYL-m-PHENYLENEDIAMINE SULPHATE) and 1-Acetoxy-2-methylnaphthalene (1-HYDROXYYETHYL-4,5-DIAMINOPYRAZOLE SULPHATE). These can be used in the molecular form or in the form of peroxide-compatible salts.

The hair colouring compositions of the present invention may also include non oxidative hair dyes i.e. direct dyes which may be used alone or in combination with the above described oxidative dyes. Suitable direct dyes include azo or anthraquinone dyes and nitro derivatives of the benzene series and mixtures thereof. Such direct dyes are particularly useful to deliver shade modification or highlights. Particularly preferred are Basic Red 51, Basic Orange 31, Basic Yellow 87 and mixtures thereof.

The hair dye compositions of the present invention will generally comprise from about 0.001% to about 10% of dyes. For example compositions providing low intensity dyeing such as natural blonde to light brown hair shades generally comprise from about 0.001% to about 5%, preferably from about 0.1% to about 2%, more preferably from about 0.2% to about 1% by weight of dyeing composition of precursors and couplers. Darker shades such as browns and black typically comprise from 0.001% to about 10% by weight, preferably from about 0.05% to about 7% by weight, more preferably form about 1% to about 5% of precursors and couplers.

Surfactants

The compositions according to the present invention may further comprise one or more surfactants. Surfactants suitable for use herein generally have a lipophilic chain length of from about 8 to about 30 carbon atoms and can be selected from anionic, nonionic, amphoteric and cationic surfactants and mixtures thereof. Preferred surfactants include non-ionic surfactants comprising one or more polyethyleneoxide chain, for example polyoxyethylene alkyl ethers or polyethyleneglycol fatty acid esters. Another preferred surfactants are alkyl ether sulphates or alkyl ether phosphates, where particularly preferable are alkyl ether phosphates having 1-20, preferably 1-10 and most preferably 1-5 ethylene oxide units. Another preferred surfactants are amphoteric surfactants, preferably betaine derivatives for example cocoamidopropyl betaine.

Any combination of surfactants can be used. Moreover, surfactants may form various micelle and liquid crystalline phases in the composition. Preferably, the surfactants will form a so-called lamellar gel network phase. The surfactants will generally be used at levels of from about 0.05% to about 30% by weight of the composition, preferably of from about 0.1% to about 15%, more preferably of from about 0.2% to about 10%.

Conditioning Agent

The compositions of the present invention may comprise or are used in combination with a composition comprising a conditioning agent. Conditioning agents suitable for use herein are selected from silicone materials, amino silicones, fatty alcohols, polymeric resins, polyol carboxylic acid esters, cationic polymers, cationic surfactants, insoluble oils and oil derived materials and mixtures thereof. Additional materials include mineral oils and other oils such as glycerin and sorbitol.

The conditioning agent will generally be used at levels of from about 0.05% to about 20% by weight of the composition, preferably of from about 0.1% to about 15%, more preferably of from about 0.2% to about 10%, even more preferably of from about 0.2% to about 2%.

Particularly useful conditioning materials are cationic polymers and silicones. Conditioners of cationic polymer type may be chosen from those already known by those skilled in the art as improving at least one cosmetic properties of keratin fibres treated with a cosmetic composition. Cationic polymers can be chosen from those comprising units of at least one amine group chosen from primary, secondary, tertiary and quaternary amine groups that may either form part of the main polymer chain, or be borne by a side substituent that is directly attached to the main polymer chain.

Silicones can be selected from polyalkylsilioxane oils, linear polydiemthylsiloxane oils containing trimethylsilyl or hydroxydimethylsiloxane endgroups, polymethylphenylsiloxane polydimethylphenylsiloxane or polydimethyldiphenylsiloxane oils, silicone resins, organofunctional siloxanes having in their general structure one or a number of organofunctional group(s), the same or different, attached directly to the siloxane chain. Said organofunctional group(s) are selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betain groups. The silicone can either be used as a neat fluid or in the form of an pre-formed emulsion.

Chelants

According to the present invention the compositions may comprise chelants. Chelants are well known in the art and refer to a molecule or a mixture of different molecules each capable of forming a chelate with a metal ion. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference.

Examples of chelants suitable for use herein include EDDS (ethylenediaminedisuccinic acid), carboxylic acids (in particular aminocarboxylic acids), phosphonic acids (in particular aminophosphonic acids) and polyphosphoric acids (in particular linear polyphosphoric acids), their salts and derivatives.

Chelants may be incorporated into the composition of the present invention as stabilizers and or preservatives. In addition it has also been found that chelants provide hair fibre damage benefits and thus they may be utilized in order to further improve the hair damage profile of the present invention. Levels of chelants in the present invention may be as low as about 0.1%, preferably at least about 0.25%, more preferably about 0.5% for the most effective chelants such as diamine-N,N'-dipolyacid and monoamine monoamide-N,N'-dipolyacid chelants (for example EDDS). Less effective chelants will be more preferably used at levels of at least about 1%, even more preferably above about 2% by weight of the composition, depending of the efficiency of the chelant.

Opacifying Agents

Suitable opacifiers may be selected from fatty alcohols, fatty acids, fatty amide derivatives, fatty esters of ethylene glycol and fatty acids of glycerol.

Solvents

Suitable solvents for use in the compositions of the present invention include, but are not limited to, water, butoxydiglycol, propylene glycol, alcohol (denat.), ethoxydiglycol, isopropylalcohol, hexylene glycol, benzyl alcohol and dipropylene glycol. Finally, the compositions according to the present invention are thus typically provided as an aqueous composition. The compositions of the present invention comprise from 10%, preferably 20%, more preferably 30%, most preferably 50% by weight of a solvent.

Method of Use

It is understood that the examples of methods of use and embodiments described herein are for illustrative purposes only and that various modifications or changes in light thereof will be suggested to one skilled in the art without departing from the scope of the present invention.

Oxidative hair dye compositions are usually sold in kits comprising, in individually packaged components such as separate containers, a dye component (also called "dye cream" for emulsions or gels or "dye liquid" for solutions) comprising the oxidative dye, precursors and alkalizing agent which is typically ammonia in a suitable carrier, and; a hydrogen peroxide component (also called "hydrogen peroxide cream" for emulsions or gels or "hydrogen peroxide liquid" for solutions or developer) comprising the oxidizing agent (usually hydrogen peroxide). The consumer mixes the dye component and hydrogen peroxide component together immediately before use and applies it onto the hair. According to the present invention the cross-linked amphoteric polymer may be comprised within the dye component, or the hydrogen peroxide component or both components. The carbonate source if present is typically present in the dye component.

Similarly, bleaching compositions are also usually sold as a kit comprising two or three individually packaged components typically in two or three separate containers. The first component comprises an alkalising agent or ammonium ion source (e.g. ammonia), the second component comprises the oxidizing agent and the third (optional) component comprises a second oxidizing agent. The bleaching compositions are obtained by mixing the above-mentioned compositions immediately before use. For hair bleaching compositions the cross linked amphoteric polymer may be comprised within any of the three components or as a separate fourth component. The carbonate source if present is typically in the alkalizing component for bleaching compositions.

After working the mixture for a few minutes (to insure uniform application to all of the hair), the oxidative dye or bleaching composition is allowed to remain on the hair for an amount sufficient for the dyeing or bleaching to take place (usually from about 2 to 60 minutes, typically about 30 to 45 minutes). The consumer then rinses his/her hair thoroughly with tap water and allows it to dry. It is then observed that the hair has changed from its original colour to the desired colour.

When present in the oxidative dye compositions and bleaching compositions, the optional conditioning agent can be provided in a third container. In the latter case, all three compositions can be mixed immediately before use and applied together, or the content of the third container can be applied (after an optional rinse step) as a post-treatment immediately after the oxidative dye composition or bleaching composition resulting from the mixture of the other containers. The cross linked amphoteroic polymer may be present in this third container.

In another embodiment of the present invention the oxidative hair dye or bleaching compositions may comprise as an optional fourth component a colour referesher composition. Such colour refresher compositions comprise at least one pre-formed dye and may be applied to the hair immediately after the oxidative colour i.e. from about 1 minute after oxidative hair dye or bleach application to 60 days after the application. These colour refresher composition can be used to increase the initial colour obtained and or boost the colour during the wash and style cycle until the next oxidative colouring or bleaching event.

The resultant mixed hair colouring or bleaching compositions according to the present invention thus have a resultant viscosity of from 1000 to 60000 cPs, preferably from 2000 to 30000 cPs and most preferably from 3000 to 25000 cPs. Moreover prior to mixing the hair dye component may have viscosity of less than 1000 cPs, such composition is often referred as "thin-thin" or "liquid" colorant. The viscosity of the resultant mixture of oxidative and dye/bleach components in other words the resultant mixed hair colouring or bleaching composition is from 1000 to 60000 cPs, preferably from 2000 to 30000, more preferably form 3000 to 25000 cPs. Viscosity is measured using Brookfield viscometers with cone and plate attachment. For viscosities in the range of 0-12000 cPs the Brookfield DV-11 viscometer with S42 plate is used. 2 ml sample of the composition is equilibrated at 26.7° C. for three minutes before the readings are taken at 1 rpm. For viscosities in the range of 12,000-50,000 cPs the Brookfield DV-1 viscometer with S52 plate is used. 0.5 ml sample of the composition is equilibrated for 1 minute at 26.7° C. before the readings are taken at 1 rpm.

According to the present invention the methods of colouring or bleaching hair also comprise embodiments whereby the composition is applied to the hair and preferably the mixture is worked for a few minutes (to insure uniform application to all of the hair). The composition is then allowed to remain on the hair in order for the colour to develop for a time period of less than about 20 minutes, preferably less than about 15 minutes, more preferably from about 5 minutes to about 10 minutes, most preferably for about 10 minutes. The consumer then rinses his/her hair thoroughly with tap water and allows it to dry and or styles the hair as usual. This method provides additional convenience to consumer by permitting faster colouring or bleaching application.

According to an alternative embodiment of the present invention, the method of colouring and or bleaching the hair is a sequential oxidative hair colouring or hair bleaching method comprising the steps of at least two sequential oxidative hair colour or hair bleaching treatments wherein the time period between each treatment is from 1 to 60 days, preferably from 1 to 40 days, more preferably from 1 to 28 days, even more preferably from 1 to 14 days and most preferably from 1 to 7 days. In such embodiments the time that the composition is retained on head may be less than about 20 minutes and is preferably less than about 10 minutes and most preferably from about 2 minutes to about 5 minutes. This method allows consumer to perform colouring or bleaching process in a way similar to conventional hair washing or conditioning process.

The kits described hereinabove are well known in the art and the composition in each container can be manufactured utilizing any one of the standard approaches. For example, polymer is added to cold water with strong agitation (strong agitation is not required if polymer supplied as emulsion or suspension) and then mixed for about 1 hour with reduced agitation and optional heating to provide full polymer dissolution or dispersion or swelling. The polymer solution may be then optionally fully or partially neutralised, achieiving collapse or maximum swelling of the microgel depending on the desired application. This polymer premix is then mixed cold with remaining amounts of water, other optional components and oxidizing agent or a source of carbonate, carbamate, hydrogencarbonate or peroxomoncarbonate ions, thus forming first or second part of the above described bleaching or colouring kit.

The present invention may be utilized in a variety of packaging and dispensing devices. These dispensing devices can come in the form of separate devices which may be used independently or in combination with one another. Typically, the hair colouring or bleaching compositions are contained within separate single or multi compartment containers so that the compositions can be stored separately from one another before use. The compositions are then mixed together by a mixing means and then applied to the consumer's hair by an application means.

The most common packaging device which can be used for the present invention involves storing the developer in a container such as a bottle, tube, aerosol, or a sachet and separately storing the dye lotion in an additional compartment within the developer container or in a separate container which may be identical such as a dual sachet or aesrosol systems for example or different such as a bottle and tube system.

The consumer may mix the developer lotion and the dye lotion by any means. This may simply involve the use of a mixing bowl into which the lotions are dispensed and then mixed, preferably using a mixing means such as a tool. Alternatively it may involve the addition of one of the lotions into the container of the other lotion, (typically the dye lotion is added to the developer lotion), followed by manual shaking or mixing with a tool. Another system involves the perforation or displacement of a seal located between the separate compartments of the dye and developer lotion within a single container or sachet followed by manual mixing within the container or in a separate and or additional container.

An example of such devices are the so called 'twist and go' devices. These devices allow the consumer to twist the base of a container holding the dye which enables a communication port to open that exposes the base of the bottle holding the dye and the top of the bottle holding the developer. The two components are mixed and the consumer dispenses the product by squeezing the flexible top portion of the bottle for dispensing.

Alternatively more complex devices may be utilised, whereby the lotions are mixed upon actuation of dispensing. An example of such a complex system is a dual aerosol system e.g. bag-in-can or piston. The dye and developer are stored separately in two aerosol cans within one device, a propellant being used to pressurize the contents of the can or bag in can or piston and a valve providing the control of dispensing. When the consumer actuates the valve, the dye and developer are dispensed simultaneously out of the cans and are mixed together via a static mixer just before dispensing the product onto the hair. The ratio of the dye and developer can be manipulated by the viscosity of the products, the can pressure, or by altering the flow channel sizes through the valve. Additionally, the product can be foamed and delivered via a mousse form.

Another example of such a complex system utilises a dual piston screw system. The dye and the developer are kept in separate piston cylinder systems within the system and when the consumer actuates a button, two screws are rotated such that the dual pistons inside pressurize the liquid in the cylinders and thus force the products to move through a mixing station and out of the nozzle for dispensing. The ratios of the dye and the developer can be manipulated by the diameter of the cylinder of the package. Additionally, an in line static mixer can be used to aid mixing and such a system can be completely disposable or completely refillable.

Yet another system utilises one or more manually actuated pumps. The product may be premixed in a collapsible sachet. When the consumer actuates the pump, the liquid inside the pump is dispensed. As the manually actuated pump returns to the upright position it forces product from a collapsible sachet. Alternatively, a dual system can be installed whereby two sachets and two pumps are used to deliver the dye and the developer lotions to the hair. Alternatively, a single pump connected to two sachets can deliver the product by incorporating the mixing point within the pump. Another embodiment uses a rigid bottle and a dip tube to connect the product to the pump system. Finally, a delaminating bottle can be used in combination with a manually actuated pump where the inner layer of the bottle separates from the outer layer of the bottle which forces the contents of the bottle to be emptied.

Typically these complex systems offer the advantage of product application independently of the orientation of the product.

The devices described herein above can also be used in combination with a product delivery and or application tool to aid application of the product onto the hair. Again these devices may be of a very simple nature such as a nozzle attached to one of the containers or a separate applicator device such as a comb or brush. Such combs and brushes can be adapted in order to achieve particular effects, whether it be quick and even coverage or root/hairline touch up, or highlights or streaks. Alternatively, the container or one of the containers may be provided with a comb attached to or instead of the dispensing nozzle whereby the product is dispensed through hollow tines and dispensing apertures located in the comb tines. The comb tines may be provided with single or multiple openings along the tines to improve product application and evenness especially root to tip. Product dispensation can be achieved by mechanical pressure applied to the container for example delaminating bottles or any of the mechanisms described hereinabove. The comb may be provided on the container such as to facilitate easy application and may be positioned vertically (so called verticomb) or at an angle to allow the consumer to access all areas. All devices may be designed to have inter-changeability, so that a range of different tools for hair application can be provided to the consumer.

The application devices may also include devices which assist in achieving particular effects such as highlighting, such as highlighting combs, brushes and tools, foils and highlighting caps.

Additional device technology can be used to assist in the penetration of the product into the hair. Examples of such technology include heating devices, ultraviolet light devices and ultrasound devices.

EXAMPLES

The following examples illustrate oxidative dye compositions according to the present invention. It is understood that the examples and embodiments described herein are for illustrative purposes only and that various modifications or changes in light thereof will be suggested to one skilled in the art without departing from the scope of the present invention.

The polymers of the invention may be prepared by conventional polymerization techniques. For example, the following process used to prepare polymer 1 of the Examples can be used:

A 500 mL three-neck round bottom flask is charged with Span 80 (1.5 g) and cyclohexane (200 g) and fitted with a mechanical paddle stirrer, a glass thermometer with Thermowatch probe, and a septum. The contents of the flask are sparged with argon for 30 minutes through an inline bubbler and a head pressure of argon maintained thereafter. A separate flask is charged with water (36.53 g), distilled acrylic acid (9.88 g, 0.137 moles), filtered MAPTAC solution (Aldrich 50 wt %, 20.17 g, 0.0457 moles), 1,3-diallylurea (0.0384 g, 0.27 mmol, 0.15 mol % of monomer), and V-50 (0.0496 g, 0.18 mmol, 0.1 mol % based on monomer). It is cooled in an ice bath and sparged with argon for 30 minutes through a 20 gauge Teflon tube. Agitation is set for 600 rpm and the monomer solution is added to the round bottom flask over 4 minutes using a 20 gauge Teflon tube. The flask was heated to 65° C. with a heating mantle for 4 hours. The reaction is cooled to 40° C. and aqueous ammonia (29%, 1.44 g, 0.0246 moles) added. The reaction is allowed to stir for at least 15 minutes after the ammonia addition and then discharged to a 500 mL separatory funnel. The lower, predominantly aqueous layer is withdrawn after 15 minutes and is allowed to air dry overnight. The polymer solids are then dried in the vacuum oven for 2 h at 50° C.

Examples 1-10

Mixed Compositions

| Ingredient | Formulation | | | | | | | | | |
|---|---|---|---|---|---|---|---|---|---|---|
| | 1 | 2 | 3 | 4 | 5 | 6 | 7 | 8 | 9 | 10 |
| Ammonium Carbonate | 4.0 | — | — | — | — | — | — | 5.0 | 3.0 | — |
| Ammonium Hydrogen Carbonate | — | 2.0 | — | — | 2.5 | 4.0 | 2.0 | — | — | 4.0 |
| Ammonium Carbamate | — | 2.0 | — | — | 2.5 | 4.0 | 2.0 | — | — | 4.0 |
| Potassium Hydrogen Carbonate | — | — | — | 5.0 | — | — | — | — | 1.5 | — |
| 28% Ammonia | — | — | 3.5 | — | — | — | — | — | — | — |
| Sodium Glycinate | — | 2.0 | 2.0 | 2.0 | 2.0 | 2.0 | 2.0 | 2.0 | 2.0 | 2.0 |
| Polymer 1 | 2.5 | — | — | 2.0 | 2.5 | 3.0 | 2.0 | 2.0 | 2.5 | 2.5 |
| Polymer 2 | — | 2.0 | — | — | — | — | — | — | — | — |
| Polymer 3 | — | — | 2.5 | — | — | — | — | — | — | — |
| Crodafos ® CES (Cetearyl alcohol, di-cetyl phosphate & ceteth-10 phosphate) | — | — | — | 2.5 | — | — | — | — | — | — |
| Ceteareth-25 | — | — | — | 0.8 | — | — | — | — | — | — |
| Sodium Lauryl Sulphate | — | — | — | — | — | — | 0.3 | — | — | — |
| Cocoamidopropyl Betaine | — | — | — | — | 1.0 | — | — | — | — | — |
| Cetyl Alcohol | — | — | — | 1.0 | — | — | 1.3 | — | — | — |
| Stearyl Alcohol | — | — | — | 1.0 | — | — | 1.3 | — | — | — |
| Ethoxydiglycol | 1.5 | 1.5 | 1.5 | — | 1.5 | 1.5 | 1.5 | 1.5 | 1.5 | 1.5 |
| Hexylene Glycol | 4.0 | 4.0 | 4.0 | — | 4.0 | 4.0 | 4.0 | 4.0 | 4.0 | 4.0 |
| Isopropyl alcohol | 2.0 | 2.0 | 2.0 | — | 2.0 | 2.0 | 2.0 | 2.0 | 2.0 | 2.0 |
| Propylene glycol | 2.0 | 2.0 | 2.0 | — | 2.0 | 2.0 | 2.0 | 2.0 | 2.0 | 2.0 |
| Sodium sulphite | 0.1 | 0.1 | 0.1 | 0.1 | 0.1 | 0.1 | 0.1 | 0.1 | 0.1 | 0.1 |
| Ascorbic Acid | 0.1 | 0.1 | 0.1 | 0.1 | 0.1 | 0.1 | 0.1 | 0.1 | 0.1 | 0.1 |
| EDTA(tetrasodium salt) | 0.1 | 0.1 | 0.1 | 0.1 | 0.1 | 0.1 | 0.1 | 0.1 | 0.1 | 0.1 |
| p-phenylene diamine | 0.8 | | 0.6 | 0.1 | 0.8 | — | 0.6 | 0.1 | 0.8 | — |

-continued

| Ingredient | Formulation | | | | | | | | | |
|---|---|---|---|---|---|---|---|---|---|---|
| | 1 | 2 | 3 | 4 | 5 | 6 | 7 | 8 | 9 | 10 |
| p-amino phenol | — | 0.3 | — | 0.4 | — | — | — | 0.4 | — | 0.3 |
| 2,5-diaminotoluene sulphate | — | 0.1 | 0.2 | — | — | — | 0.2 | — | — | 0.1 |
| m-aminophenol | 0.2 | — | 0.1 | — | 0.2 | — | 0.1 | — | 0.2 | — |
| Resorcinol | — | 0.5 | — | 0.4 | — | — | — | 0.4 | — | 0.5 |
| napthol | 0.03 | — | 0.2 | — | 0.03 | — | 0.2 | — | 0.03 | — |
| 4-amino-2-hydroxy toluene | — | 0.2 | — | 0.3 | — | — | — | 0.3 | — | 0.2 |
| Phenyl methyl pyrazalone | 0.2 | — | — | — | — | — | — | — | — | — |
| 1-hydroxyethyl-4,5-diamino pyrazole sulphate | 0.3 | — | — | — | — | — | — | — | — | — |
| Basic red 51 | — | 0.1 | — | — | — | — | 0.2 | — | — | — |
| Basic yellow 87 | — | 0.2 | — | — | — | — | 0.3 | — | — | — |
| Hydrogen Peroxide (35% active) | 8.6 | 8.6 | 8.6 | 13.0 | 13.0 | 17.0 | 13.0 | 10.7 | 10.7 | 10.7 |
| Polyquaternium-22 (Merquat ® 295) | — | — | — | — | 0.20 | — | — | — | — | — |
| Polyquaternium-37 & Mineral oil (Salcare ® SC95) | 0.25 | — | — | — | 0.25 | — | — | — | 0.25 | — |
| Amodimethicone (DCAP 6087) | — | — | — | 1.0 | — | — | — | — | — | — |
| pH adjust to pH 9.0 | qs | qs | qs | qs | qs | qs | qs | qs | qs | qs |
| Water | qs | qs | qs | qs | qs | qs | qs | qs | qs | qs |

The viscosity of these compositions are within the range of from 1000 to 60000 cPs.

Examples 11-12

Tint and Developer Compositions

| | Example 11 Liquid formulation | | Example 12 Cream formulation | |
|---|---|---|---|---|
| Ingredient | Part 1 (Dye) | Part 2 (Hydrogen peroxide) | Part 1 (Dye) | Part 2 (Hydrogen pero |
| Ammonium Carbonate | 10.0 | — | 10.0 | — |
| Sodium Glycinate | 4.0 | — | 4.0 | — |
| Polymer 1 | — | 4.0 | 3.0 | — |
| Crodafos ® CES (Cetearyl alcohol, di-cetyl phosphate & ceteth-10 phosphate) | — | — | 4.0 | — |
| Ceteareth-25 | — | — | — | 1.8 |
| Cocoamidopropyl Betaine | 1.5 | — | — | — |
| Cetyl Alcohol | — | — | — | 2.1 |
| Stearyl Alcohol | — | — | — | 2.1 |
| Ethoxydiglycol | 3.0 | — | — | — |
| Hexylene Glycol | 8.0 | — | — | — |
| Isopropyl alcohol | 4.0 | — | — | — |
| Propylene glycol | 4.0 | — | — | — |
| Sodium sulphite | 0.2 | — | 0.2 | — |
| Ascorbic Acid | 0.3 | — | 0.3 | — |
| EDTA (tetrasodium salt) | 0.1 | 0.05 | 0.05 | 0.05 |
| p-phenylene diamine | 0.8 | — | 0.6 | — |
| 2,5-diaminotoluene sulphate | — | — | 0.2 | — |
| m-aminophenol | 0.2 | — | 0.1 | — |
| napthol | 0.03 | — | 0.2 | — |
| Phenyl methyl pyrazalone | 0.2 | — | — | — |
| 1-hydroxyethyl-4,5-diamino pyrazole sulphate | 0.3 | — | — | — |
| Hydrogen Peroxide (35% active) | — | 8.6 | — | 13.0 |
| Polyquaternium-37 & Mineral oil (Salcare ® SC95) | — | 0.25 | 0.5 | — |
| pH adjust to | 9.0 | 2.5 | 9.0 | 2.5 |
| Water | qs | qs | qs | qs |

The viscosity of part 1 and 2 in example 11 is less than 1000 cps and thus can be used as a so called thin-thin composition. Part 1) and Part 2) are mixed prior to application on hair and the viscosity of the mixed formulations is within the range of 1000 to 60000 cPs.

Polymer 1 in the above examples contains 75 mol % acrylic acid, 24.85 mol % 3-methacryloylaminopropyl trimethylammonium chloride and 0.15 mol % 1,3-diallylurea.

Polymer 2 in the above examples contains 70 mol % acrylic acid, 29.3 mol % diallyldimethylammonium chloride and 0.70 mol % 1,3-diallylurea.

Polymer 3 in the above examples contains 70 mol % acrylic acid, 29.36 mol % 3-methyl-1-vinylimidazolim chloride and 0.64 mol % 1,3-diallylurea.

When used in part 2 of the compositions the polymers may be optionally partially neutralized to achieve minimum viscosity for the use in the so called thin-thin systems. The preferred neutralizing agent is aqueous ammonia.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair colouring or bleaching composition comprising at least one oxidizing agent and at least one cross-linked amphoteric polymer, wherein said polymer comprises
   1) at least one first monomer of formula (I)

$$R_1\text{—}CH\text{=}CR_2\text{—}CO\text{—}Y_1 \quad (I)$$

where $R_1$ is independently selected from the group consisting of a hydrogen atom, a methyl radical and a COOH group, $R_2$ is independently selected from the group consisting of a hydrogen atom, a methyl radical and a $CH_2COOH$ group, and $Y_1$ is independently selected from an OH group or a $NHC(CH_3)_2CH_2SO_3H$ group,
   2) at least one second monomer selected from diallyldimethylammonium salt, 3-methyl-1-vinylimidazolium salt, or the monomers of formula (II)

$$R_3\text{—}CH\text{=}CR_4\text{—}CO\text{—}Y_2\text{—}(C_nH_{2n})\text{—}N^+(R_5R_6R_7)A^- \quad (II)$$

wherein $R_3$ and $R_4$, which are identical or different, are each selected from a hydrogen atom or a methyl radical; $R_5$, $R_6$ and $R_7$, which are identical or different, are each selected from a linear or branched alkyl radical having from 1 to 6 carbon atoms; $Y_2$ is selected from an NH group or an oxygen atom; n is an integer from 2 to 5; and $A^-$ is an anion selected from anions derived from organic or inorganic acids and
   3) at least one cross-linking agent, wherein said polymer comprises from about 40 mol/% to about 80 mol/% of said first monomer, from about 20 mol/% to about 60 mol/% of said second monomer, and from about 0.01 mol/% to about 5 mol/% of said cross linking agent.

2. A hair colouring or bleaching kit comprising
   i) an individually packaged oxidizing component comprising at least one source of hydrogen peroxide and
   ii) an individually packaged second component comprising at least one cross-linked amphoteric polymer, wherein said polymer comprises
   1) at least one monomer of formula (I)

$$R_1\text{—}CH\text{=}CR_2\text{—}CO\text{—}Y_1 \quad (I)$$

where $R_1$ is independently selected from the group consisting of hydrogen atom, a methyl radical and a COOH group, $R_2$ is independently selected from the group consisting of a hydrogen atom, a methyl radical and a $CH_2COOH$ group, and $Y_1$ is independently selected from an OH group or a $NHC(CH_3)_2CH_2SO_3H$ group,
   2) at least one monomer selected from diallyldimethylammonium salt, 3-methyl-1-vinylimidazolium salt, or the monomers of formula (II)

$$R_3\text{—}CH\text{=}CR_4\text{—}CO\text{—}Y_2\text{—}(C_nH_{2n})\text{—}N^+(R_5R_6R_7)A^- \quad (II)$$

wherein $R_3$ and $R_4$, which are identical or different, are each selected from a hydrogen atom or a methyl radical; $R_5$, $R_6$ and $R_7$, which are identical or different, are each selected from linear or branched alkyl radical having from 1 to 6 carbon atoms; $Y_2$ is selected from an NH group or an oxygen atom; n is an integer from 2 to 5; and $A^-$ is an anion selected from anions derived from organic or inorganic acids and
   3) at least one cross-linking agent, wherein said polymer comprises from about 40 mol/% to about 80 mol/% of said first monomer, from about 20 mol/% to about 60 mol/% of said second monomer, and from about 0.01 mol/% to about 5 mol/% of said cross linking agent.

3. A hair colouring or bleaching kit comprising
   i) an individually packaged oxidizing component comprising
      a) at least one source of hydrogen peroxide, and
      b) at least one cross-linked amphoteric polymer, wherein said polymer comprises
      1) at least one monomer of formula (I)

$$R_1\text{—}CH\text{=}CR_2\text{—}CO\text{—}Y_1 \quad (I)$$

where $R_1$ is independently selected from the group consisting of hydrogen atom, a methyl radical and a COOH group, $R_2$ is independently selected from the group consisting of a hydrogen atom, a methyl radical and a $CH_2COOH$ group, and $Y_1$ is selected from an OH group or a $NHC(CH_3)_2CH_2SO_3H$ group,
      2) at least one monomer selected from diallyldimethylammonium salt, 3-methyl-1-vinylimidazolium salt, or the monomers of formula (II)

$$R_3\text{—}CH\text{=}CR_4\text{—}CO\text{—}Y_2\text{—}(C_nH_{2n})\text{—}N^+(R_5R_6R_7)A^- \quad (II)$$

wherein $R_3$ and $R_4$, which are identical or different, are each selected from a hydrogen atom or a methyl radical; $R_5$, $R_6$ and $R_7$, which are identical or different, are each selected from linear or branched alkyl radicals having from 1 to 6 carbon atoms; $Y_2$ is selected from an NH group or an oxygen atom; n is an integer from 2 to 5; and $A^-$ is an anion selected from anions derived from organic or inorganic acids
      3) at least one cross-linking agent, wherein said polymer comprises from about 40 mol/% to about 80 mol/% of said first monomer, from about 20 mol/% to about 60 mol/% of said second monomer, and from about 0.01 mol/% to about 5 mol/% of said cross linking agent, and
   ii) an individually packaged second component comprising a source of carbonate ions, carbamate ions, hydrogencarbonate ions, or mixtures thereof, wherein the composition formed upon mixing said components comprises at least 0.1 mol/l of a source of carbonate ions, carbamate ions, hydrogencarbonate ions, peroxymonocarbonate ions, or mixtures thereof.

4. A hair colouring or bleaching composition according to claim 1, wherein said composition further comprises at least one opacifier selected from the group consisting of fatty alcohols, fatty acids, fatty amide derivatives, fatty esters of ethylene glycol, fatty acids of glycerol, and mixtures thereof.

5. A hair colouring or bleaching composition according to claim 1, wherein said composition has a viscosity of from about 1000 cPs to about 60000 cPs.

6. A hair colouring or bleaching composition according to claim 1, wherein said composition further comprises a conditioning active.

7. A hair colouring or bleaching composition according to claim 1, wherein said composition further comprises at least one oxidative dye precursor or at least one pre-formed dye.

8. A method of colouring and or bleaching hair comprising the steps of applying a composition according to claim 1 on the hair, leaving said composition on the hair for up to about 60 minutes and subsequently rinsing said composition from the hair.

9. A method according to claim 8, wherein said composition is retained on the hair for a time period of less than about 20 minutes.

10. A method of sequential oxidative hair colouring or hair bleaching comprising the steps of at least two sequential oxidative hair colour or hair bleaching treatments wherein the time period between each treatment is from about 1 day to about 60 days, and wherein each treatment comprises the steps of providing a composition according to claim 1, applying said composition to the hair and retaining said composition on the hair for a time period of less than about 20 minutes and subsequently rinsing said composition from the hair.

11. A hair colouring composition according to claim 1, wherein said composition further comprises at least about 0.1 mol/l of a source of carbonate ions, carbamate ions, hydrogencarbonate ions, peroxymonocarbonate ions, or mixtures thereof 12. A hair colouring or bleaching composition according to claim 1, wherein said composition further comprises at least one source of ammonium ions.

13. A hair coloring or bleaching composition according to claim 1, wherein said composition has a pH of from about 7.5 to about 9.3.

14. A hair coloring or bleaching composition according to claim 1, wherein said composition further comprises at least one source of radical scavenger.

15. A hair coloring or bleaching composition according to claim 1, wherein said at least one first monomer is selected from acrylic acid, methacrylic acid, or mixtures thereof.

16. A hair coloring or bleaching composition according to claim 1, wherein said at least one second monomer is selected from the group consisting of diallyldimethylammonium chloride, 3-methyl- 1 -vinylimidazolium chloride, 3- methylacryolylamidopropylthrimethylammonium chloride, and mixtures thereof.

17. A hair coloring or bleaching composition according to claim 1, wherein said at least one cross-linking agent is selected from the group consisting of 1,3- diallylurea, N,N-diallylacrylamide, N,N-methylenebisacrylamide, pentaerythritol triallylether, triallylamine, tetraallylammonium chloride, methyltriallylammonium chloride, and mixtures thereof.

18. A hair coloring or bleaching composition according to claim 1, wherein said at least one first monomer is selected from acrylic acid or methacrylic acid, said at least one second monomer is selected from diallyldimethylammonium chloride or 3-methylacryolamidopropylthrimethylammonium, and said cross-linking agent is 1,3- diallylurea.

19. A hair colouring or bleaching composition according to claim 1, wherein said composition comprises from about 0.1% to about 20% by weight of said at least one cross-linked amphoteric polymer.

* * * * *